United States Patent
Mazzucco et al.

(10) Patent No.: US 6,699,283 B2
(45) Date of Patent: Mar. 2, 2004

(54) HEART VALVE WITH RECTANGULAR ORIFICE

(76) Inventors: Daniel Clarke Mazzucco, 90 Windsor Rd., Medford, MA (US) 02155; Christopher Allan Hartemink, 479 Commonwealth Ave., Boston, MA (US) 02215; Seth Owen Newburg, 15 Harrington St., Newton, MA (US) 02460-1525

( * ) Notice: Subject to any disclaimer, the term of this patent is extended or adjusted under 35 U.S.C. 154(b) by 0 days.

(21) Appl. No.: 10/132,440

(22) Filed: Apr. 25, 2002

(65) Prior Publication Data

US 2002/0161432 A1 Oct. 31, 2002

Related U.S. Application Data

(60) Provisional application No. 60/286,861, filed on Apr. 26, 2001.

(51) Int. Cl.$^7$ .................................................. A61F 2/24
(52) U.S. Cl. .................... 623/2.33; 623/2.2; 623/2.27; 623/2.34
(58) Field of Search .............................. 623/2.2, 2.22, 623/2.25, 2.28, 2.3, 2.31, 2.32, 2.33, 2.26, 2.27

(56) References Cited

U.S. PATENT DOCUMENTS

| | | | |
|---|---|---|---|
| 19,323 A | | 2/1858 | Williams |
| 3,546,711 A | | 12/1970 | Bokros |
| 3,579,642 A | * | 5/1971 | Heffernan et al. ............ 623/2.4 |
| 3,689,942 A | * | 9/1972 | Rapp .................................. 3/1 |
| 3,835,475 A | | 9/1974 | Child |
| 3,938,197 A | | 2/1976 | Milo |
| 4,078,268 A | | 3/1978 | Possis |
| 4,159,543 A | | 7/1979 | Carpentier |
| 4,276,658 A | | 7/1981 | Hanson et al. |
| 4,306,319 A | | 12/1981 | Kaster |
| 4,352,211 A | | 10/1982 | Parravicini |
| 4,451,937 A | | 6/1984 | Klawitter |
| 4,655,772 A | | 4/1987 | De Liotta et al. |
| 4,820,299 A | | 4/1989 | Philippe et al. |
| 5,207,707 A | | 5/1993 | Gourley |
| 5,628,791 A | | 5/1997 | Bokros et al. |
| 5,843,183 A | | 12/1998 | Bokros et al. |
| 6,059,826 A | | 5/2000 | Bokros et al. |
| 6,206,918 B1 | * | 3/2001 | Campbell et al. .......... 623/2.32 |
| 6,395,025 B1 | * | 5/2002 | Fordenbacher et al. .... 623/2.28 |

* cited by examiner

*Primary Examiner*—Bruce Snow
*Assistant Examiner*—Cheryl Miller

(57) ABSTRACT

A mechanical heart valve prosthesis has a generally rectangular orifice and two leaflets that move between a closed position nearly perpendicular to blood flow and an open position nearly parallel to blood flow. Due to the uniform dimension of a rectangle, the leaflets are hinged at the periphery of the orifice, and present a single large central flow region to the blood when opened. The base provides several means of constraining the leaflet rotation during opening and closing.

5 Claims, 6 Drawing Sheets

HEART VALVE WITH RECTANGULAR ORIFICE

CROSS-REFERENCE TO RELATED APPLICATIONS

This application is entitled to the benefit of Provisional Patent Application Ser. No. 60/286,861, filed Apr. 26, 2001.

STATEMENT REGARDING FEDERALLY SPONSORED R & D

Not applicable.

REFERENCE TO SEQUENCE LISTING

Not applicable.

BACKGROUND

1. Field of Invention

The present invention relates to mechanical heart valve prostheses, and, in particular, to a bileaflet prosthetic heart valve with a rectangular orifice and periphery that enable full leaflet opening for improved blood flow with a single central orifice.

2. Description of Prior Art

A wide variety of heart valve prostheses have been developed to operate hemodynamically in conjunction with the pumping action of the heart to replace defective natural valves. These valves generally have annular valve bodies that function with a single occluder or a plurality of occluders that allow forward blood flow through the valve during systole and prevent retrograde flow during diastole.

The first successful mechanical heart valves were caged ball valves, pioneered by Starr and Edwards, based on the ball valve of U.S. Pat. No. 19,323 (Williams, 1858). The hemodynamic concept of the single tilting disk valve is an improvement over the caged ball valve because it reduces energy loss, and therefore it largely replaced the caged ball implant. U.S. Pat. No. 3,546,711 (Bokros, 1968) discloses a single tilting disk heart valve with journaled hinges set away from the orifice wall. U.S. Pat. No. 3,835,475 (Child, 1974) discloses a free-floating disk that is constrained by projections. U.S. Pat. No. 4,306,319 (Kaster, 1981) discloses a tilting disk heart valve with an oval, egg, or kidney shaped disk and orifice. In this valve, the disk is hinged with an axis of rotation across the largest dimension of the orifice. The tilting disk heart valves have improved flow characteristics over the caged ball valves, but still partially obstruct the central flow of blood while open.

Bileaflet valves were designed to be an improvement over the tilting disk valves; they open more smoothly, close more reliably, and have a lower profile. U.S. Pat. No. 4,078,268 (Possis, 1976) discloses a bileaflet valve with hinge axes slightly offset from the orifice diameter. U.S. Pat. No. 4,159,543 (Carpentier, 1976) discloses a bileaflet valve with diametric hinge axes in which the leaflets rotate about physical axles. U.S. Pat. No. 4,276,658 (Hanson, 1980) discloses a manifestation of a bileaflet valve where the leaflets have convex ears that fit into concave sockets for pivoting. U.S. Pat. No. 4,352,211 (Parravicini, 1981) discloses a design in which the leaflets are arcuate cylindrical shells contoured to match the round aortic duct. U.S. Pat. No. 4,451,937 (Klawitter, 1982) discloses a design with ear-guided hinges, in which the leaflets are constrained by protuberances. U.S. Pat. No. 4,655,772 (De Liotta, 1985) discloses a bileaflet design in which the leaflets are mounted on hook guides. The shift from the caged ball or tilting disk valve designs to the bileaflet designs was an improvement in safety, efficacy, and efficiency. However, bileaflet valve designs still partially obstruct the blood flow when the leaflets are open.

In an effort to decrease central occlusion, trileaflet valves have been developed. U.S. Pat. No. 4,820,299 (Phillippe, 1986) discloses a trileaflet design with hinge axes disposed from the center of the orifice at a distance that is 75 percent of the radius of the base. U.S. Pat. No. 5,207,707 (Gourley, 1993) discloses another trileaflet valve with ear-guided leaflets and conical stops. U.S. Pat. No. 5,628,791 (Bokros, 1997) discloses a trileaflet valve with another design for the hinge guidance projections. U.S. Pat. No. 5,843,183 (Bokros, 1998) discloses a trileaflet design with projection stops, as well as a significantly orifice-reducing contour to provide additional stops. U.S. Pat. No. 6,059,826 (Bokros, 2000) discloses a design with tapered leaflets to reduce cavitation in the blood.

U.S. Pat. No. 3,938,197 (Milo, 1976) discloses a valve with a pentagonal orifice mounted in a circular ring and five roughly triangular leaflets. This valve has no central occlusion, but has a significantly reduced orifice area as well as an excess of moving parts.

A major drawback of existing mechanical heart valves is the risk of thrombus formation on the valve that can foul the mechanism. Additionally, such thrombi can embolize and lead to medical conditions such as stroke, heart attack, and pulmonary embolism. Thrombosis occurs when blood is damaged by shear forces on blood corpuscles, by turbulent flow, or by chemical interactions with synthetic materials, all of which are exacerbated by cardiovascular implants. Presently, mechanical heart valve recipients receive anticoagulant drug therapy in order to avoid thrombus formation; however, this drug therapy introduces a new set of comparable health risks. Reducing the blood damage caused by the valve has the benefit of lowering the required levels of anticoagulants needed to prevent thrombosis.

Shear forces and turbulence are generated as a result of a velocity gradient in the fluid flow. In unobstructed ducted flow, the fluid velocity is a maximum in the center of the duct, and is zero at the boundary. If the occluder mechanism of a valve lies in the central region of flow when the valve is open, its surfaces induce drag on the high velocity fluid causing additional shear forces and turbulence in the fluid. With the exception of U.S. Pat. No. 3,938,197 (Milo, 1976) this is the case in all of the heart valve designs in the prior art listed above. Some valve designs move the occluders out of the direct center of flow when the valve is open by employing three or more leaflets; however, there is still significant flow occlusion. Additionally, these designs increase the number of moving parts, which, in turn, increases the probability of mechanical failure.

The use of synthetic materials such as pyrolytic carbon that have high durability and reasonably low thrombogenicity is known to the prior art. Such materials have effectively minimized material-induced thrombosis.

SUMMARY

In accordance with the present valve, a heart valve prosthesis comprises an annular body that encloses an orifice that is generally rectangular in cross-section and leaflets that open to allow forward blood flow and close to prevent retrograde flow. The axes of rotation of the leaflet hinges are near the periphery of the orifice.

Objects and Advantages

Accordingly, the primary objects of this valve are: first, to remove central flow obstructions in the valve orifice through geometric optimization; second, to obviate the need for small side orifices that split flow; third, to maximally size leaflets, limiting the required number to two; and fourth, to maintain orifice area by obviating irregular leaflet contours, taking advantage of the uniform geometry of the rectangle. These objects result in numerous advantages, detailed below, which provide a superior flow dynamic compared to the prior art. This superior flow dynamic reduces stress placed on the heart and damage to the blood, which, in turn, reduces the burden of anticoagulation therapy and the risk of thrombosis to the patient.

There are guidelines that can be used to evaluate and compare valve designs. The primary four design principles for replacement heart valves are: (1) energetic efficiency, (2) embolism prevention, (3) reduction of turbulence, and (4) reduction of blood trauma. Other principles such as noise reduction, sterilization, and material biocompatibility have largely been standardized.

These four principles deal with reducing damage to the heart (1) and blood (2–4). The major drawback of mechanical valves, vis a vis bioprosthetic valves, is that patients require anti-coagulation therapy. The dosage and frequency of this treatment attempts to minimize the competing morbidity and mortality due to stroke (too little anti-coagulant) and due to hemorrhage (too much anti-coagulant). The present valve is based on the realization that placing the leaflets in a central location has deleterious effects on all four design principles, which stem from one central cause: dividing blood flow.

Comparing energetic efficiency of valves addresses principle (1). Flow without obstructions is more efficient than flow with obstructions, and flow through a smaller orifice is less efficient than flow through a larger orifice. All surfaces provide no-slip boundaries, so two offset central leaflets have four drag surfaces, whereas two peripheral leaflets have only two drag surfaces presented to the flow. Additionally, these drag surfaces in the central case are located such that they stop the flow where it would otherwise be fastest and most efficient. In contrast, the two drag surfaces in the peripheral case are located where the flow velocity would be close to zero in the absence of leaflets, so there is little loss of efficiency.

Effective orifice area is another primary measure of valve efficiency. Due to flow mechanics, the simple act of dividing a circular viscid flow into two equal sub-flows doubles the resistance, despite the same nominal cross-sectional area. Considering the simplified geometries of a bileaflet circle, an inscribed trileaflet circle, an inscribed pentaleaflet circle, and this rectangular valve mounted in the same orifice perimeter, the normalized effective area of flow is 1.0 for the rectangular valve, 0.64 for the bileaflet, 0.56 for the trileaflet, and 0.75 for the pentagon. Each physical manifestation of these shapes has complex irregularities that affect flow efficiency, but the inherent geometric disadvantages are dominant factors.

The second result of central flow obstruction is shear damage. Clotting is the chief drawback of mechanical heart valves, in accordance with principle (2) above. One of the primary mechanisms by which valves exacerbate clotting is by inducing high shear rates. When blood shears and blood cells are ruptured, not only is the oxygen carrying capacity of blood diminished, but the damaged cells also release chemical factors that trigger coagulation. Of the shapes listed above, the rectangular orifice again proves to be most advantageous with regard to shear because its flow is most uniform. In order to pass the same flow though the effectively smaller orifices of the bi-, tri-, and pentaleaflet valves, the blood must achieve a higher peak velocity in the center of each separate sub-flow. This leads to a multiplicative effect: the peak velocity has increased, and the distance over which the blood velocity must transition from no-slip to peak had diminished. Thus shear has increased significantly, and blood is increasingly damaged.

In the final comparison of this design with the prior art in light of the above design principles, other aspects of geometry can contribute to blood trauma. The rectangular design has the shortest length of edges presented to the blood. Leaflet edges lead to turbulent energy dissipation (3) and physical crushing of blood cells between impacting surfaces (4). Additionally, the present valve does not sacrifice the number of leaflets. This valve could function with one leaflet, but the closing times and forces would increase. The prior art demonstrates that with these factors in mind, a bileaflet design is an improvement over a single-leaflet design. However, increasing the number of leaflets increases the number of parts, which increases the risk of mechanical failure. In addition, more leaflets increase the risk of performance failure, and leaflet closure complications can be catastrophic. Any damage to a leaflet that might impair simultaneous closing leads to regurgitation, which stresses the heart. Hence increasing the number of leaflets beyond two incurs additional risk that has not yet been shown to provide concomitant benefit for patients.

Taking all four of these principles into account, the rectangular valve reflects a revolutionary shift in valve design, akin to the step from caged ball to tilting disk, and from tilting disk to bileaflet.

DRAWING FIGURES

Figure 1:
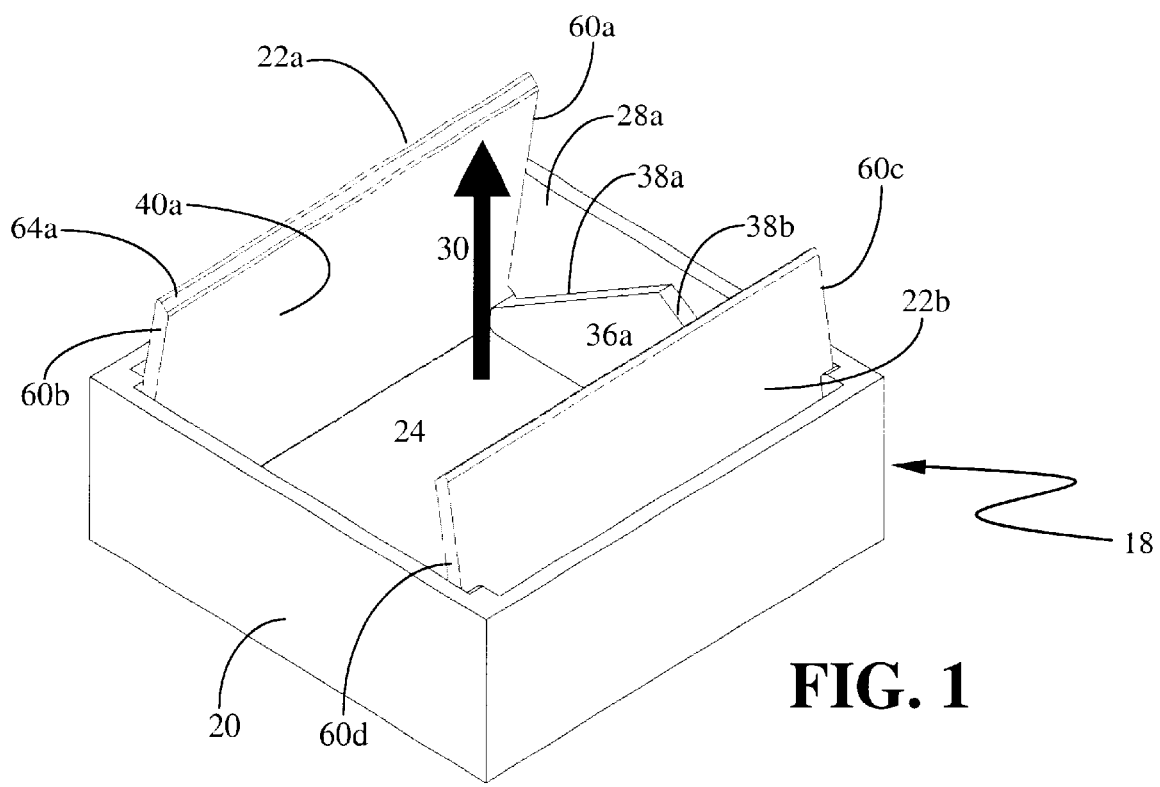
FIG. 1 is a perspective view from downstream of a preferred embodiment of the present valve, with leaflets in maximally open position.

REFERENCE NUMERALS IN DRAWINGS valve 18
base 20
leaflets 22a, 22b
orifice 24
internal back walls 26a, 26b
internal side walls 28a, 28b
flow 30
sockets 32a, 32b, 32c, 32d
ears 34a, 34b, 34c, 34d
shelves 36a, 36b
closing stops 38a, 38b, 38c, 38d underside 40a of leaflet 22a
underside 40b of leaflet 22b
protrusions 42a, 42b
opening stops 44a, 44b, 44c, 44d
top side 46a of leaflet 22a
top side 46b of leaflet 22b
arcuate end 48 of socket 32
proximal socket wall 50 of socket 32
distal socket wall 52 of socket 32
bearing surface 54
convex surface 56 of ear 34
planar surfaces 58 of ear 34
side surfaces 60a, 60b of leaflet 22
back surface 62a of leaflet 22a
back surface 62b of leaflet 22b
mating surface 64a of leaflet 22a
mating surface 64b of leaflet 22b
transition tubes 66, 68
groove 70
retaining ring 72
hemi-sections 74a, 74b
flange 76
slot 78
leading edge 80
trailing edge 82
distal end 84 of transition tube 66
distal end 90 of transition tube 68
proximal end 86 of transition tube 66
proximal end 88 of transition tube 68
male marge 92 of hemi-section 74
female marge 94 of hemi-section 74
sewing rings 96a and b

DESCRIPTION

FIG. 1 through FIG. 6

Preferred Embodiment

Figure 2:
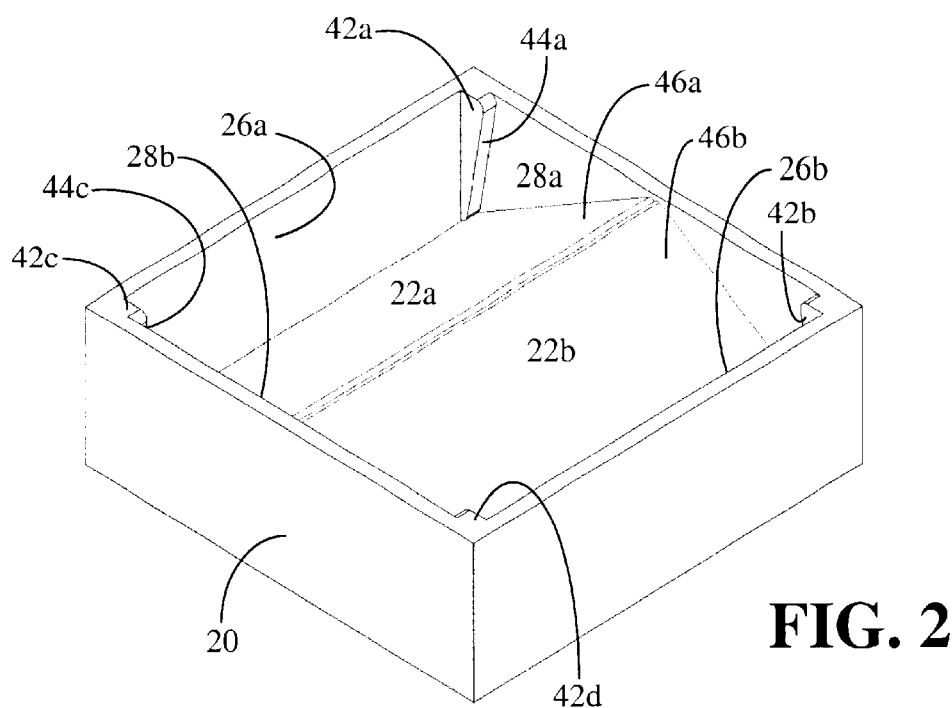
FIG. 2 is a perspective view from downstream of the embodiment of FIG. 1, with leaflets in maximally closed position.

Referring now to FIG. 1 and FIG. 2, there is shown a preferred embodiment of the present valve which is a valve 18 formed of a base 20 and leaflets 22a and 22b. The base 20 is a generally rectangular member whose internal back walls 26a and 26b and internal side walls 28a and 28b define the orifice 24 and enclosed blood passageway. The arrow shows the general direction of blood flow 30.

Figure 3:
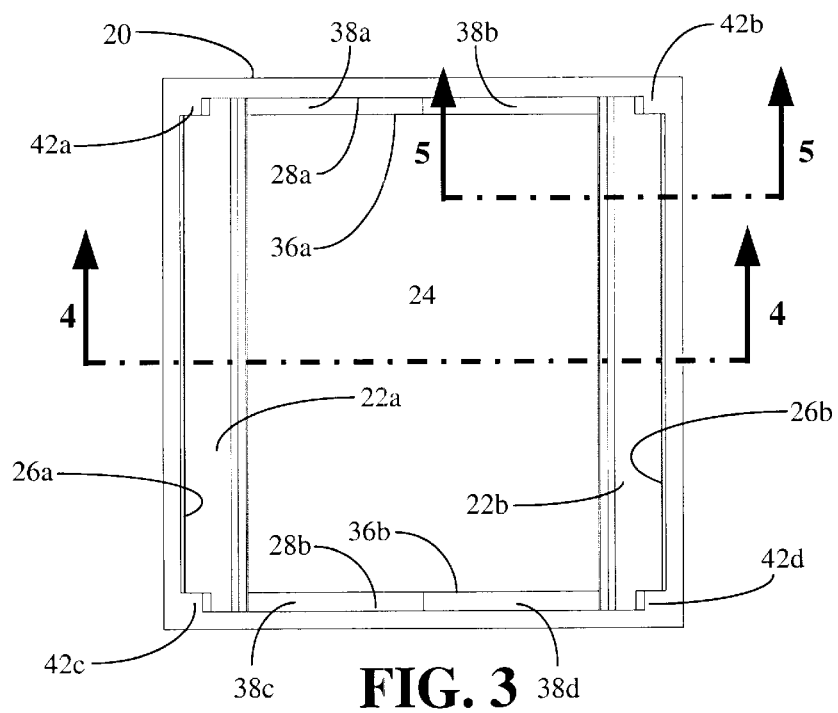
FIG. 3 is a direct view from downstream of the embodiment of FIG. 1, with leaflets in maximally open position.

Referring now to FIG. 3, there is shown a direct view of valve 18 from downstream of the embodiment of FIG. 1. Shown are shelves 36a and 36b that project from internal side walls 28a and 28b forming closing stops 38a and 38b. Protrusions 42a, 42b, 42c, and 42d project from side walls 28a and 28b forming opening stops 44a, 44b, 44c, and 44d.

Figure 4:
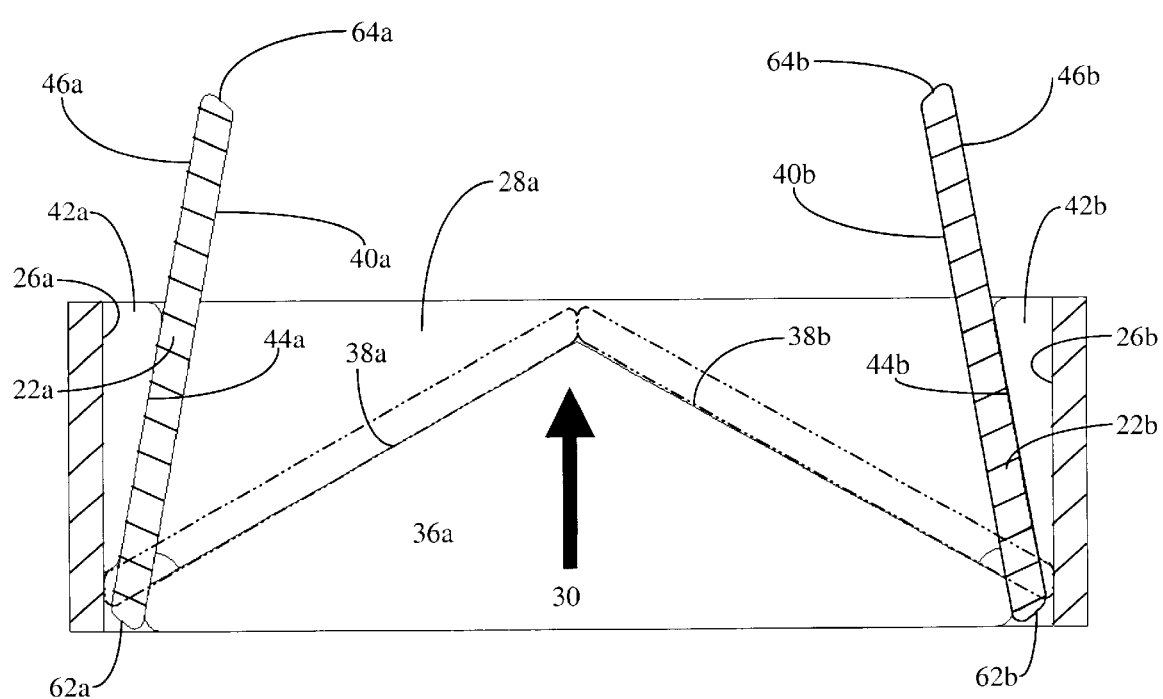
FIG. 4 is a cross-section taken along the line 4—4 in FIG. 3.

Referring now to FIG. 4, there is shown a cross-section taken along the line 4—4 in FIG. 3. Leaflets 22 are shown in open position, and are also indicated in closed positions by phantom lines. Shelf 36a forms closing stops 38a and 38b to mate with undersides 40a and 40b of leaflets 22 limiting leaflet rotation in closure. Protrusions 42a and 42c form opening stops 44a and 44c to mate with top side 46a of leaflet 22a to limit leaflet rotation in opening. In this manner, leaflets 22 move to open positions without occluding flow, as depicted in FIG. 2. Internal side wall 28a (shown in FIG. 4) and internal side wall 28b (not shown in FIG. 4) are identical with opposite orientation.

Figure 5:
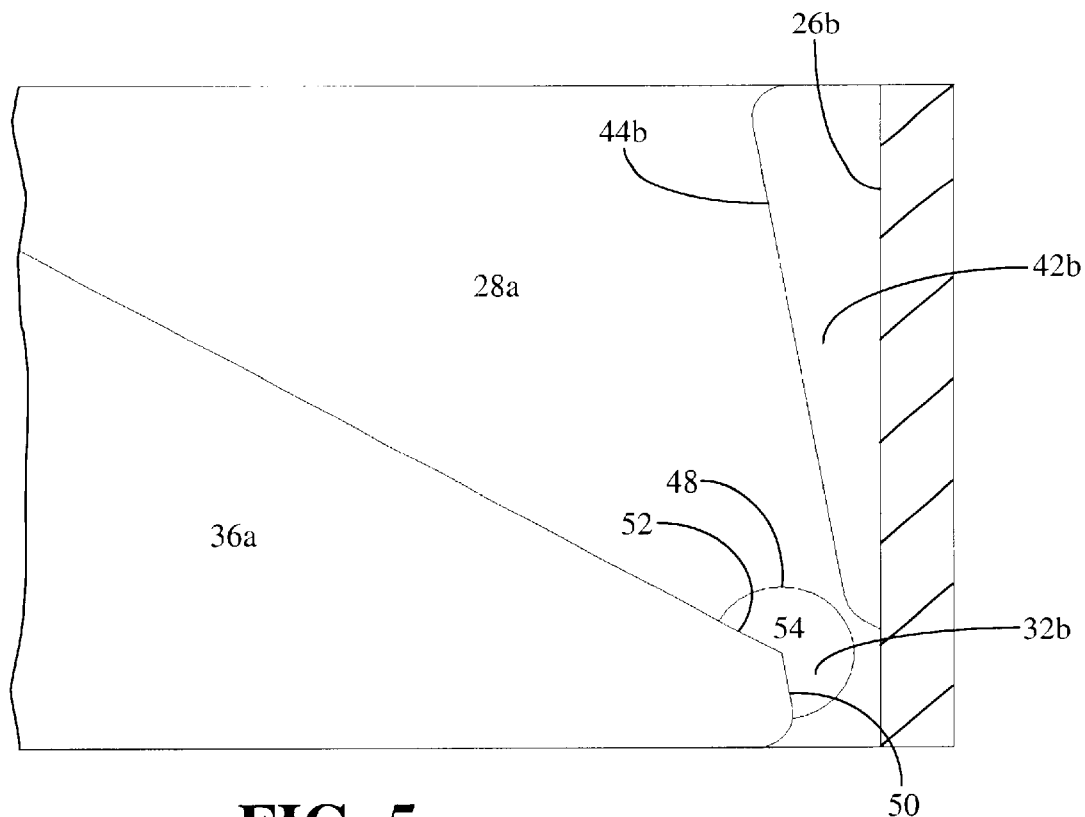
FIG. 5 illustrates a portion of the embodiment of FIG. 1, and is a cross-section taken along the line 5—5 in FIG. 3.

Referring now to FIG. 5, there is shown a portion of the embodiment of FIG. 1 with leaflets 22 removed to reveal the mechanism of sockets 32. Sockets 32 are formed as recesses within internal side walls 28, having an arcuate end 48 joined with proximal socket wall 50 and distal socket wall 52 to form a bearing surface 54. Bearing surface 54 is a surface of revolution. Sockets 32a, 32b, 32c, and 32d, cooperate with ears 34a, 34b, 34c, and 34d, respectively, attached to leaflets 22 to allow pivotal movement of leaflets 22 between the positions illustrated in FIG. 1 and FIG. 2. Except for their orientation within internal side walls 28, sockets 32 are identical.

Figure 6:
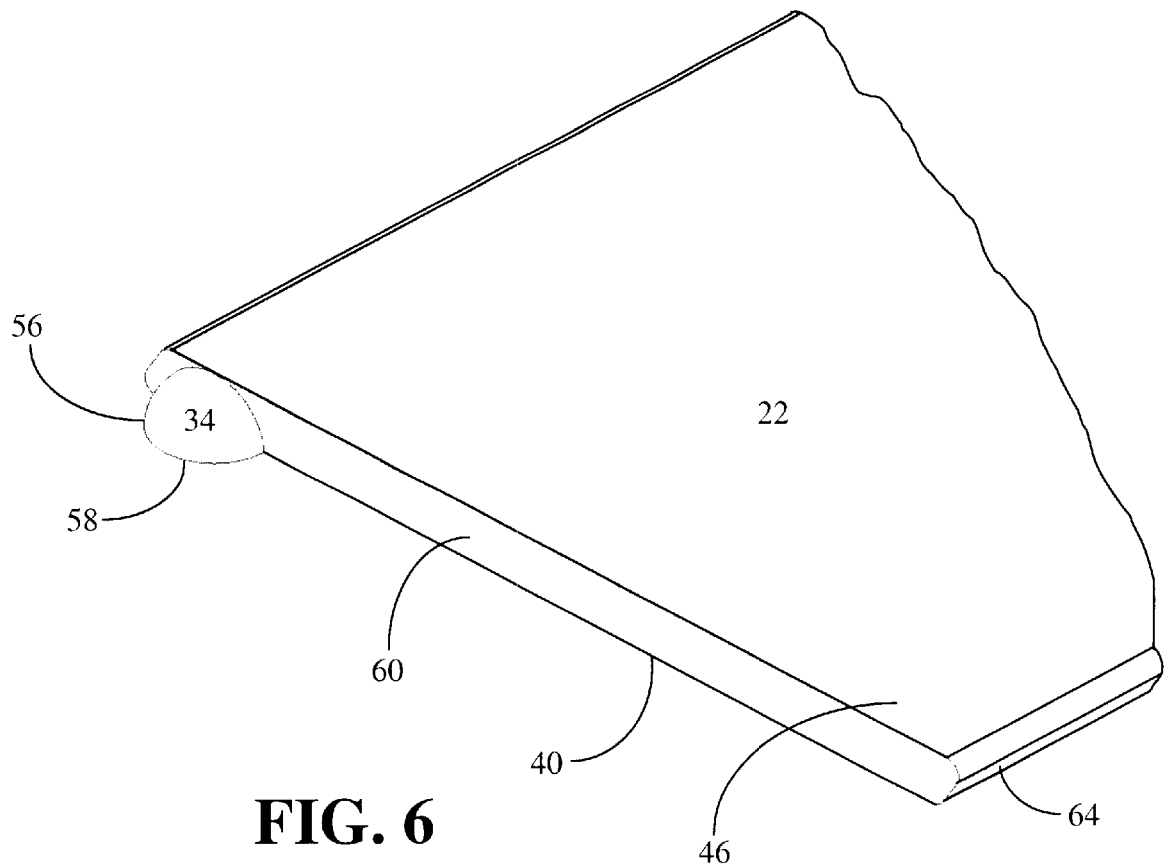
FIG. 6 illustrates a portion of the embodiment of FIG. 1.

Referring now to FIG. 6, there is shown a portion of a preferred embodiment of leaflets 22, which are identical to each other and symmetric such that the edge not shown mirrors the edge shown. Motion of leaflets 22 is defined by a pivot axis defined by ears 34 that are shaped as partial sections of spheres, thus having a convex surface 56 and a flat surface 58. The diameter of ears 34 closely approximates, but is slightly smaller than, the diameter of bearing surfaces 54, thus allowing ears 34 to extend into the recesses forming sockets 32 for pivotal movement therein. Ears 34 engage bearing surfaces 54 during movement of leaflets 22 between open and closed positions to maintain leaflets in position while the potential for jamming is reduced. The distance between side surfaces 60a and 60b, and between 60c and 60d, of leaflets 22 is approximately equal to the distance between internal side walls 28a and 28b such that, when ears 34 are within sockets 32, leaflets 22 are held securely in position. In a preferred embodiment, ears 34 extend beyond side surfaces 60 of leaflets 22 by an amount less than the depth of bearing surface 54, thereby cooperating with internal side walls 28, and reducing the tendency for jamming between ears 34 and bearing surface 54.

Either or both of internal side walls 28 may be adapted to serve as stops for leaflets 22 by limiting motion of leaflets 22. That is, as illustrated in FIG. 4 and FIG. 5, proximal socket walls 50 may be positioned to prevent movement of leaflets 22 past the illustrated open position by engagement with planar surfaces 58 of ears 34. An additional stop in the closed position may be provided by further engagement of back surfaces 62 of leaflets 22 with internal back walls 26 as illustrated by the phantom lines in FIG. 4. Mating surface 64a of leaflet 22a cooperates with mating surface 64b of leaflet 22b when leaflets are in closed position.

It is known in the prior art that a hemocompatible coating can be added to a substrate to make strong, highly-wear-resistant, biocompatible valve bodies and leaflets. The fabrication of the substrate and coating, using substrate comprising monolithic carbon or titanium, and coating comprising pyrolytic carbon or silicone, is known to the prior art.

Operation

Hereafter, certain parts of the preceding description are taken up again so to relate them to the operation of the valve.

When the heart contracts in systole, a pressure gradient exists in the forward direction. This pressure gradient creates a moment about the hinge axes, which are located along the periphery of the flow. This moment forces leaflets 22 to the open position. Leaflets 22 are restrained from detachment by ears 34 on side surfaces 60 of leaflets 22 and sockets 32 on internal side walls 28. Leaflets 22 open until they encounter one or more steric obstructions employed by valve 18; namely, protrusions 42 in base 20 that impact the top sides 46 of leaflets 22, and proximal walls 50 in hinge sockets 32 that impact planar surfaces 58 of ears 34. These stops can be designed to stop leaflets 22 at any angle, such that leaflets 22 open as widely as possible while still providing adequate exposure of top sides 46 of leaflets 22 to retrograde blood flow for closure moments. The angle from the transverse valve plane would be approximately 70 to 90 degrees.

When leaflets 22 are open, there is only one orifice 24 and the orifice area is maximal so blood flows efficiently: flow resistance, turbulence, and shear damage are minimal. Additionally, the placid region behind leaflets 22, when open, well emulates the aortic sinus that is critical for coronary artery function.

When the heart rests in diastole, a pressure gradient exists in the retrograde direction. This pressure gradient creates a moment about the hinge axes. This moment forces leaflets 22 to the closed position. Leaflets 22 close until they encounter one or more steric obstructions employed by the valve; namely, distal socket walls 52 in hinge sockets 32 opposing planar surfaces 58 of ears 34, shelves 36 in base 20 opposing undersides 40 of leaflets 22, mating surfaces 64 of leaflets 22 opposing each other, and back surfaces 62 of leaflets 22 opposing internal back walls 26 of base 20. These stops can be designed to stop leaflets 22 at any angle, such that leaflets 22 seal the orifice as quickly as possible. The angle from the transverse valve plane would be approximately 0 to 45 degrees.

Figure 9:
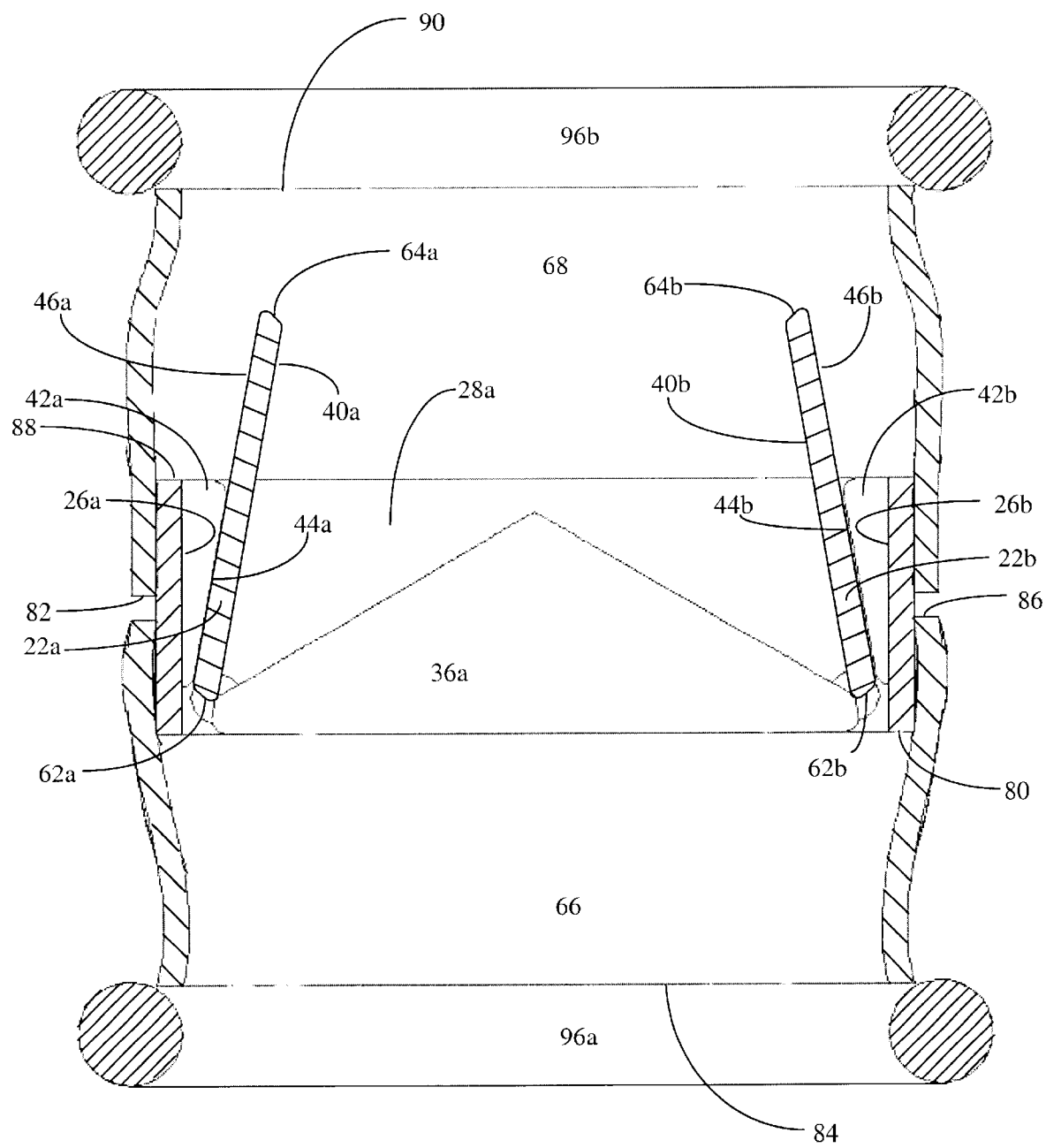
FIG. 9 is a cross-section taking along the line 4—4 in FIG. 3 showing an optional sewing ring.

Implantation of replacement heart valves can be performed by techniques well known to the prior art using means such as a sewing ring 96a and 96b as shown in FIG. 9. Heart tissue is malleable, and few deleterious effects should arise from the minor deformation necessary to accommodate a non-circular valve with appropriate perimeter. Should modified implantation be necessary, an adaptor is illustrated as an additional embodiment that could conjoin the round valve annulus and the rectangular replacement base.

FIG. 7 and FIG. 8

Additional Embodiments

Figure 7:
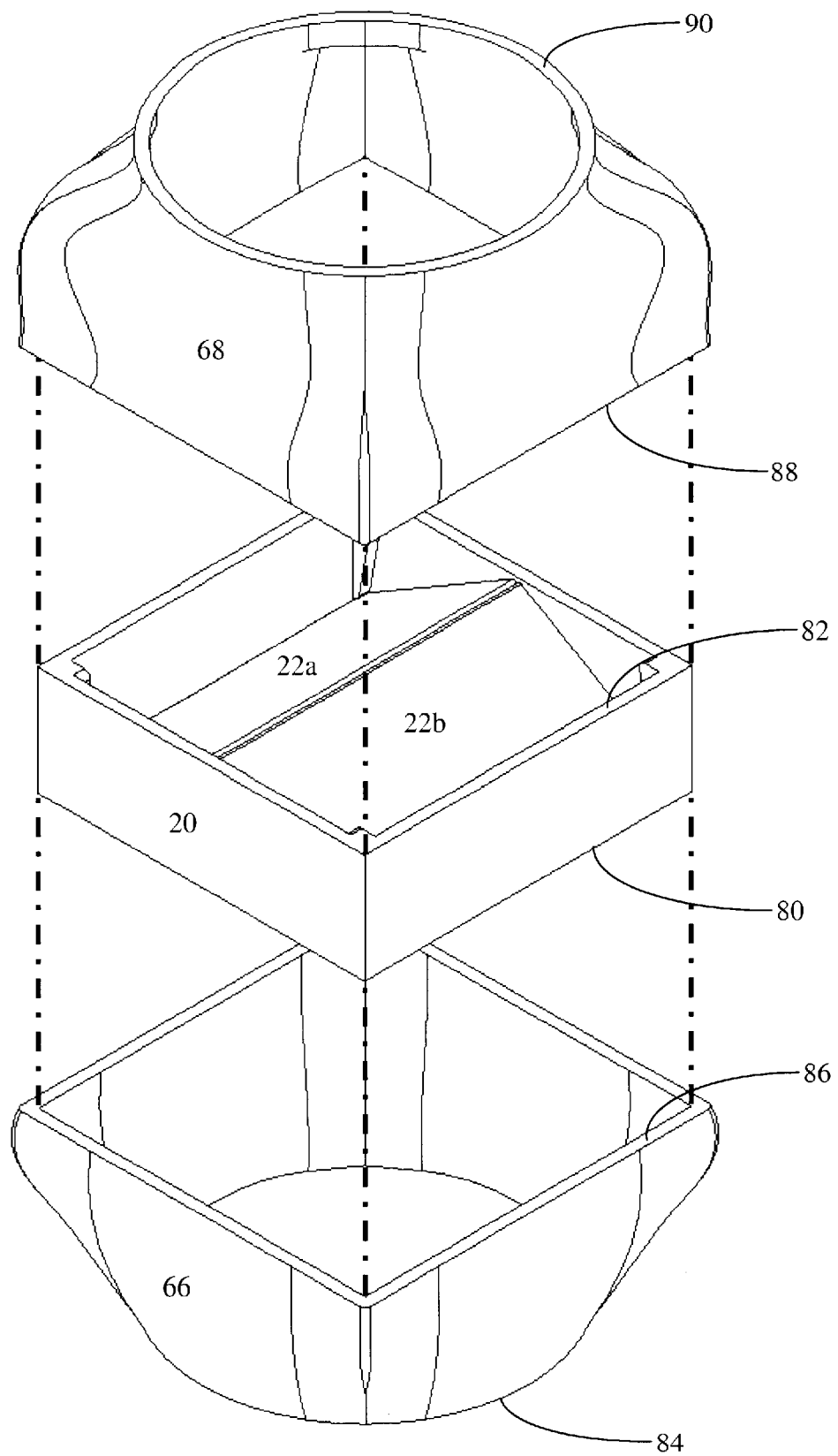
FIG. 7 is an exploded perspective view of an additional embodiment of the present valve.

In the event that the cardiac or arterial tissue cannot endure the trauma of deformation from its biological shape to the rectangular geometry of the base during attachment, methods for attaching the valve to cardiac or arterial tissue are provided. Referring to FIG. 7, there is shown an exploded perspective view of an additional embodiment of the present valve, with projection lines indicating alignment of exploded parts. Transition tubes 66 and 68 are attached to the base 20 of the valve 18 at the leading edge 80 and trailing edge 82, respectively. Transition tubes 66 and 68 are tubular structures having rectangular annuli on the ends adjacent to valve 18, or proximal ends 86 and 88. The cross-section of transition tubes 66 and 68 gradually taper to circular annuli at surfaces distant from valve 18, which are distal ends 84 and 90. Distal ends 84 and 90 can be sutured or otherwise attached to biological tissue without deforming the tissue, and rectangular proximal ends 86 and 88 can be sutured, glued, or otherwise attached to the compatible rectangular annulus of the valve 18. The transition tubes 66 and 68 may be fabricated from a variety of materials; in the present embodiment the transition tubes 66 and 68 are made of woven polyester fibers. Either transition tube 66 or transition tube 68 could be used without the other if surgically preferable.

Figure 8:
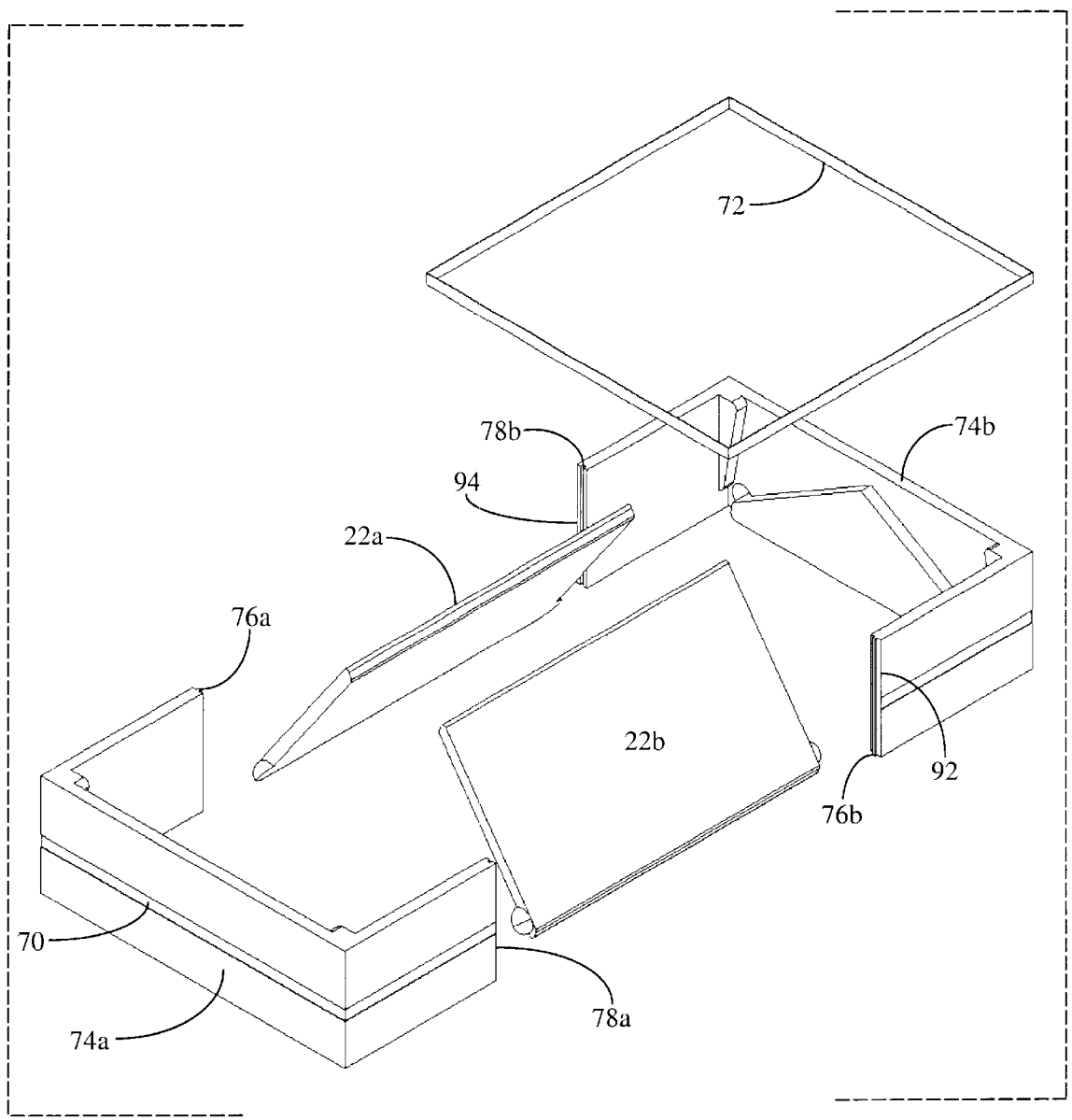
FIG. 8 is an exploded perspective view of a second additional embodiment of the present valve.

Now giving consideration to assembly of the valve, if brittle materials are used to make the base that do not permit elastic deformation of the valve components, the base may be constructed of multiple pieces that are assembled with the leaflets to form the complete valve. With reference to FIG. 8, there is shown an exploded perspective view of an additional embodiment of the present valve, representing one possible means of assembly. Base 20 is split into two identical hemi-sections 74a and 74b. Hemi-sections 74a and 74b each have a male marge 92 with a flange 76 and a female marge 94 with a slot 78. When aligned, flange 76a of hemi-section 74a complements slot 78b of hemi-section 74b and flange 76b of hemi-section 74b complements slot 78a of hemi-section 74a. Thus, leaflets 22 can be inserted between separated hemi-sections without being deformed, and base 20 is subsequently united. A multitude of mating methods known to the art may be used other than the slot and flange described here. A retainer ring 72 is seated in a grove 70 and binds hemi-sections 74a and 74b and leaflets 22a and 22b in the final assembly. Other means of attachment such as glue or screws may be used to bind hemi-sections 74a and 74b and leaflets 22a and 22b in the final assembly.

Conclusion, Ramifications, and Scope

The rectangular heart valve described here affords multiple benefits over the prior art. Due to the uniform dimension of the rectangle, the hinge axes are positioned at the periphery of the orifice and still open to a position nearly parallel to blood flow. This creates one large central orifice, which creates numerous advantages, including an increase in effective orifice area, a reduction of turbulence, a reduction of flow impedance, and a reduction of shear, which reduces blood damage and the need for anti-coagulation therapy for the patient.

As is clear from the foregoing, the valve is in no manner limited to those of its preferred embodiment or modes of construction and application which have been described more explicitly; it embraces, on the contrary, all the variants thereof which may occur to the mind of a technician skilled in the manner, without departing from the scope and spirit of the present valve.

For example, on the rectangular orifice and leaflets there will be some amount of rounding of corners, both for manufacturing as well as implantation. Thus "rectangular" refers to any shape with four sides arranged in pairs, of which both pairs of opposing sides are substantially parallel, and the second pair of opposing sides is substantially perpendicular to the first. This concept holds true even if there is significant rounding of corners between the four sides, or other corner contouring. Additionally, the sides may be more complicated than simple line segments but still have a sense of being substantially parallel within the spirit of the valve. The leaflets would be designed to fit the shape of the orifice.

Additionally, although the preferred embodiment uses two leaflets in order to minimize closing time and design complexity, the number of leaflets can be smaller or larger than two. In particular, the geometry permits one leaflet hinged peripherally, affording the same hemodynamic benefits when open as the preferred embodiment.

Additionally, although the preferred embodiment positions the leaflets directly abutting the base to maximize central orifice area, the leaflets can be moved slightly away from the walls in order to provide a small side flow to wash the leaflet surfaces. This shunt flow would be negligible and would not compromise the hemodynamic advantages of the single central orifice of this valve.

Additionally, although the initial use for this valve might be for aortic valve replacements, it can be employed to replace any heart valve.

Additionally, although the preferred embodiment of the base is of one-piece construction, the form and operation of the valve are independent of its manufacturing, and alternate methods of manufacturing may be employed. Although one additional embodiment shows a specific mechanism for attaching two base sections, other forms of fabrication or assembly are possible.

Additionally, an internal rectangular orifice can be employed with bases of variously-shaped external peripheries. One such embodiment is the design of a round base with a rectangular orifice, which still utilizes the improved hemodynamics provided by the present valve.

Additionally, although the preferred embodiment illustrates many possible mechanisms for the constraint of leaflet rotation, the design may employ any subset of these, or others.

It is therefore to be understood, that within the scope of the appended claims, the valve may be practiced otherwise than as specifically described.

What is claimed is:

1. A heart valve prosthesis comprising:
    a. a base including a blood passageway that is substantially rectangular,
    b. a means for regulating flow comprising at least one leaflet, wherein the shape of at least one of said at least one leaflet is substantially rectangular,
    c. a means for maintaining said regulating means, wherein said maintaining means comprises one or more sockets, whereby said heart valve prosthesis permits said regulating means to open, enabling substantially central forward blood flow.

2. The prosthesis of claim 1, wherein axes of rotation of said at least one leaflet are adjacent to the contour of said base, such that, in the open position, said at least one leaflet abut said base.

3. The prosthesis of claim 2, wherein said axes of rotation of at least one leaflet are located a predetermined distance away from said base, permitting washing of tops of said at least one leaflet in the open position.

4. The prosthesis of claim 1, wherein said at least one leaflet is prevented from opening beyond a predetermined angle due to steric stop means within said one or more sockets.

5. The prosthesis of claim 1, wherein said at least one leaflet is prevented from closing beyond a predetermined angle due to steric stop means within said one or more sockets.

* * * * *